United States Patent [19]

Tamura et al.

[11] Patent Number: 4,857,544
[45] Date of Patent: Aug. 15, 1989

[54] 27-HALO DERIVATIVES OF LL-F28249 COMPOUNDS

[75] Inventors: Susan Y. Tamura, Hamilton Square; Goro Asato, Titusville, both of N.J.

[73] Assignee: American Cyanamid Company, Stamford, Conn.

[21] Appl. No.: 22,906

[22] Filed: Mar. 6, 1987

[51] Int. Cl.$^4$ .............................................. A61K 35/66
[52] U.S. Cl. ..................................... 514/450; 549/264
[58] Field of Search ......................... 549/264; 514/450

[56] References Cited

U.S. PATENT DOCUMENTS 4,584,314  4/1986  Burckhardt .......................... 549/264

Primary Examiner—Glennon H. Hollrah
Assistant Examiner—Amelia A. Owens
Attorney, Agent, or Firm—Estelle J. Tsevdos

[57] ABSTRACT

The present invention relates to novel derivatives of LL-F28249 compounds wherein the pendent C(26,27) olefinic group at C(25) is converted into a 27-bromo or 27-chloro-26-methylene group. The 27-bromo compounds are derived by reacting the LL-F28249 compounds or 5-0-trisubstituted silyl LL-F28249 compounds with N-bromoacetamide or N-bromosuccinimide in aqueous acetone, followed by desilylation for silylated LL-F28249 intermediates. The 27-chloro compounds are prepared by reacting LL-F28249 compounds with N-chlorosuccinimide in methanol. These novel halo compounds have anthelmintic, ectoparasitic, insecticidal, nematicidal and acaricidal activity and are also useful intermediates for the preparation of other novel biologically active compounds. Compositions containing the present compounds as active ingredients thereof are presented.

23 Claims, No Drawings

27-HALO DERIVATIVES OF LL-F28249 COMPOUNDS

BACKGROUND OF THE INVENTION

The present invention relates to new 27-halo derivatives of the compounds collectively defined as LL-F28249. These LL-F28249 antibiotics preferably are produced by the fermentation of the microorganism *Streptomyces cyaneogriseus* subspecies *noncyanogenus* deposited in the NRRL under deposit accession No. 15773. The morphological characteristics, compounds and method for their production are disclosed in European Patent Application No. 170,006, incorporated herein by reference thereto.

The LL-F28249 components are complex macrolids which have 5 olefinic bonds. The selective halogenation, preferably bromination or chlorination, at the $C_{27}$ of the C(26,27) double bond is the subject matter of the present patent application. These halogen derivatives have a high degree of anthelmintic, ectoparasitic, insecticidal, acaricidal and nematicidal activity and, therefore, are useful in the prevention, control or treatment of infections or infestations in warm-blooded animals and agricultural crops.

Further, the present compounds also are useful intermediates for the preparation of other novel antiparasitic, insecticidal and nematicidal compounds.

SUMMARY OF THE INVENTION

The present invention provides novel $C_{27}$ halo, bromo or chloro, derivatives of the compounds designated LL-F28249α, β, ε, ζ, θ and ι.

The LL-F28249 compounds have the following structural formula:

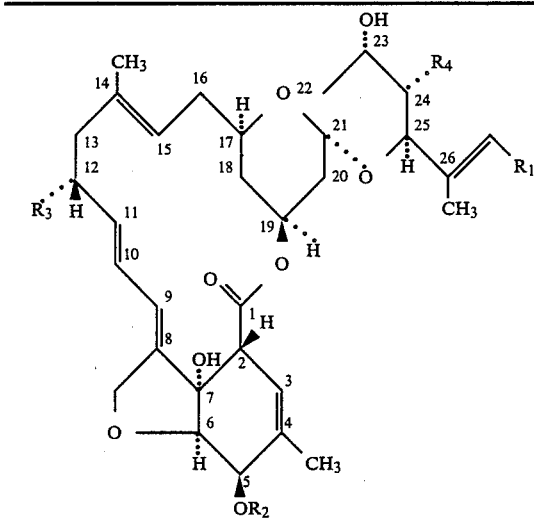

| Component | $R_1$ | $R_2$ | $R_3$ | $R_4$ |
|---|---|---|---|---|
| LL-F28249α | $CH(CH_3)_2$ | H | $CH_3$ | $CH_3$ |
| LL-F28249β | $CH_3$ | H | $CH_3$ | $CH_3$ |
| LL-F28249ε | $CH(CH_3)_2$ | H | H | $CH_3$ |
| LL-F28249ζ | $CH_2CH_3$ | H | $CH_3$ | $CH_3$ |
| LL-F28249θ | $CH(CH_3)_2$ | H | $CH_3$ | $CH_2CH_3$ |
| LL-F28249ι | $CH(CH_3)_2$ | H | $CH_2CH_3$ | $CH_3$ |

The compounds of the present invention are useful anthelmintics, ectoparasiticides, insecticides, acaricides and nematicides in treating, preventing or controlling such diseases in warm-blooded animals, such as poultry, cattle, sheep, swine, rabbits, horses, dogs, cats and human beings and agricultural crops.

Although these diseases have been recognized for years and therapies exist for the treatment and prevention of the diseases, the present invention provides novel compounds in the search of more effective therapy for such diseases. For instance, U.S. application for patent Ser. Nos. 907,283, 907,188, 907,281, 907,259, 907,187 and 907,284 of Asato and Asato et al, filed on Sept. 12, 1986 and incorporated herein by reference thereto provide compounds for such treatments. Also U.S. application for patent Ser. Nos. 022,846, 022,847, 022,848, 022,849 and 022,850 of Asato et al, filed concurrently herewith and incorporated herein by reference thereof provide compounds for such treatment.

U.S. Pat. No. 3,950,360, Aoki et al, Apr. 13, 1976 discloses certain antibiotic substances obtained by culturing a Streptomyces microorganism, said compounds being useful as insecticides and acaricides. Further, an entire series of U.S. patents relates to certain compounds produced by the fermentation of *Streptomyces avermitilis* (U.S. Pat. No. 4,171,314, Chabala et al, Oct. 16, 1979; U.S. Pat. No. 4,199,569, Chabala et al, Apr. 22, 1980; U.S. Pat. No. 4,206,205, Mrozik et al, June 3, 1980; U.S. Pat. No. 4,310,519, Albers-Schonberg, Jan. 12, 1982; U.S. Pat. No. 4,333,925, Buhs et al, June 8, 1982). U.S. Pat. No. 4,423,209, Mrozik, Dec. 27, 1983 relates to the process of converting some of these less desirable components to more preferred ones. Finally, British Patent Application No. 2166436 A discloses antibiotics also, as does Belgium Patent Application No. 904,709A.

The present compounds or the pharmaceutically and pharmacologically acceptable salts thereof exhibit excellent and effective treatment, prevention and/or control of these serious diseases of warm-blooded animals.

It is an object of the present invention, therefore, to provide novel 27-halo derivatives of LL-F28249. It is a further object to provide 27-bromo and/or 27-chloro derivatives of LL-F28249. Further, it is an object of this invention to provide a process for the preparation of these derivatives and to provide methods for preventing, treating or controlling endo and ectoparasitic (collectively parasitic) insects, nematodes, acarid and helmintic diseases and infestations in warm-blooded animals and agricultural crops by providing compositions containing prophylactically, therapeutically or pharmaceutically-effective amounts of the present novel compounds. Another objective of these compounds is as intermediates for the preparation of other novel antiparasitic and insecticidal compounds.

These and other objects of the invention will become apparent by the more detailed description of the invention provided hereinbelow.

DETAILED DESCRIPTION OF THE INVENTION

The compounds of the present instant invention are represented by the following structural formula,

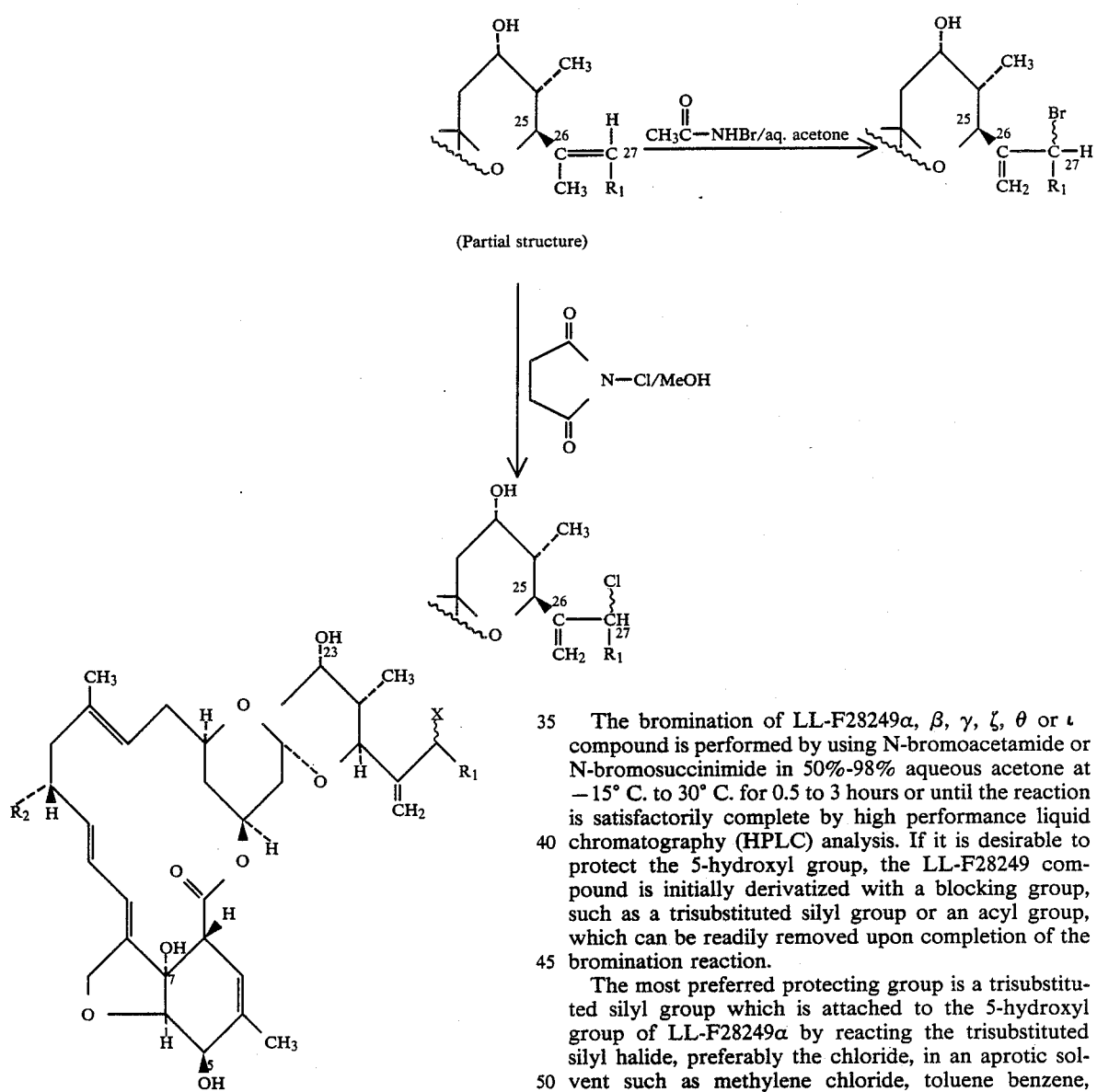

wherein, X is halogen; $R_1$ is methyl or isopropyl; and $R_2$ is hydrogen, methyl or ethyl.

A preferred group of compounds of structure (I) include X as bromine or chlorine; $R_1$ as isopropyl or methyl; and $R_2$ as hydrogen, methyl or ethyl. The most preferred group is $R_1$ as isopropyl; $R_2$ as methyl; and x as bromine or chlorine.

The bromo and chloro compounds of the present invention are prepared by reacting the appropriate LL-F28249 compound with hypobromite or hypochlorite generated in situ, using N-bromoacetamide or N-bromosuccinimide in aqueous acetone and N-chlorosuccinimide in methanol, respectively. Other halogenation procedures are available, as recognized by those skilled in the art.

In addition to the 23-hydroxy, further substitutions, such as ethers and/or esters at position 23, are readily synthesized and included within the scope of the present invention.

The overall process are schematically shown hereinbelow.

The bromination of LL-F28249α, β, γ, ζ, θ or ι compound is performed by using N-bromoacetamide or N-bromosuccinimide in 50%-98% aqueous acetone at −15° C. to 30° C. for 0.5 to 3 hours or until the reaction is satisfactorily complete by high performance liquid chromatography (HPLC) analysis. If it is desirable to protect the 5-hydroxyl group, the LL-F28249 compound is initially derivatized with a blocking group, such as a trisubstituted silyl group or an acyl group, which can be readily removed upon completion of the bromination reaction.

The most preferred protecting group is a trisubstituted silyl group which is attached to the 5-hydroxyl group of LL-F28249α by reacting the trisubstituted silyl halide, preferably the chloride, in an aprotic solvent such as methylene chloride, toluene benzene, ethylenedichloride, ethyl acetate, tetrahydrofuran or dimethylformamide in the presence of an acid acceptor such as pyridine, triethylamine, imidazole or the like. The preferred silyl group is the t-butyldimethylsilyl group. The silyl protecting group is removed by stirring the protected compound in methanol with a catalytic amount of an acid, preferably a sulfonic acid such as p-toluenesulfonic acid at 0°-50° C. for 0.5-8 hours, or by using acetic acid at room temperature.

The chlorination of LL-F28249α, β, ε, ζ, θ or ι compound is performed by using N-chlorosuccinimide in an alcohol, such as methanol, ethanol or isopropanol, at 0° C. to 50° C.

The compounds disclosed in this invention are useful as anthelmintics, ectoparasiticides, insecticides, acaricides and nematicides in human and animal health and in agriculture. These compounds may be administered orally or parenterally for human and animal health use, while in agriculture they may be applied in solid or liquid formulation.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are most prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The 27-bromo or -chloro-LL-F28249 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp., in cattle, Gastrophilus in horses, and Cuterebra sp., in rodents.

The compounds of the present invention also are useful in treating, preventing or controlling parasites which infect human beings as well. The most common genera of parasites of the gastrointestinal tract of man are Ancylostoma, Necator, Ascaris, Strongyloides, Trichinella, Capillaria, Trichuris and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola sp., carpet beetle, Attagenus sp., and the housefly Musca domestica.

Insect pests of stored grains such as Tribolium sp., Tenebrio sp., and of agricultural plants such as spider mites (Tetranychus sp.), aphids (Acyrthiosiphon sp.), southern army worms, tobacco budworms, boll weevils, migratory orthopterans such as locusts and immature stages of insects living on plant tissue are controlled by the present compounds, as well as control of soil nematodes and plant parasites such as Meloidogyne sp., which may be of importance in agriculture.

These compounds may be administered orally or parenterally for animal and human usage, while they may be formulated in liquid or solid form for agricultural use. Oral administration may take the form of a unit dosage form such as a capsule, bolus or tablet, or as a liquid drench where used as an anthelmintic in mammals.

The animal drench is normally a solution, suspension or dispersion of the active ingredient, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight. Capsules and boluses comprise the active compound admixed with a carrier vehicle such as starch, talc, magnesium stearate, or di-calcium phosphate.

Where it is desired to administer the (27-halo)27-bromo or -chloro-LL-F28249 derivatives in a dry, solid unit dosage form, capsules boluses or Where it is desired to administer the (27-halo)27-bromo or -chloro-LL-F28249 derivatives in a dry, solid unit dosage form, capsules boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the active present compound depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separated. Alternatively, the active compounds of the present invention may be administered to animals parenterally, for example, by intraruminal, intramuscular, intratracheal or subcutaneous injection. In such event, the active compound is dissolved or dispersed in a liquid carrier vehicle.

For parenteral administration, the active compound is suitably admixed with an acceptable vehicle, preferably of the vegetable oil variety such as peanut oil, cotton seed oil and the like. Other parenteral vehicles such as organic preparations using solketal, glycerol formal, and aqueous parenteral formulation also are used. The active compound or compounds of the present invention are dissolved or suspended in the parenteral formulation for administration. Such formulations generally contain about 0.005% to 5%, by weight, of the active compound.

Although the compounds of the present invention are primarily used in the treatment, prevention or control of helminthiasis, they also are useful in the prevention and treatment of diseases caused by other parasites. For example, arthropod parasites such as ticks, lice, fleas, mites and other biting insects in domesticated animals and poultry are controlled by the present invention. These compounds also are effective in treatment of parasitic diseases that occur in other animals including human beings. The optimum amount to be employed for best results will, of course, depend upon the particular compound employed, the species of animal to be treated and the type of severity of parasitic infection of infestation. Generally, the amount useful in oral administration of these novel compounds is about 0.001 mg per kg to 10 mg per kg of animal body weight, such total dose being given at one time or in divided doses over a relatively short period of time such as 1-5 days. The preferred compounds of the invention give excellent control of such parasites or animals by administering about 0.025 mg per kg to 3 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster sheels, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing about 0.005% to 2.0% by weight of the active compound are particularly suitable as feed premixes.

Feed supplements, which are fed directly to the animal, contain about 0.0002% to 0.3% by weight of the active compounds. Such supplements are added to the animal feed in an amount to give the finished feed the concentration of active compound desired for the treatment and control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds also may be administered by pouring on the skin of animals via a solution. Generally, the active compounds are dissolved in suitable inert solvents, such as dimethylsulfoxide, propylene glycol or the like, alternatively in combination of solvents, for the pour-on administration.

The compounds of this invention also are useful in combating agricultural pests the inflict damage growing or stored crop. The present compounds are applied, using known techniques as sprays, dusts, emulsions and the like, to the growing or stored crops to effect protection from such agricultural pests.

The present invention is illustrated by the following examples which are illustrative of said invention and not limitative thereof.

EXAMPLE 1

27-bromo-26-methylene-LL-F28249α

In 2.5 mL of 80% aqueous acetone, 101.7 mg of LL-F28249α is stirred at 0° C. under $N_2$, and 29.6 mg of N-bromoacetamide in 3 mL of acetone is added dropwise. After stirring for 2 hours at 0° C., the solution is diluted with 25 mL of $Et_2O$ and then washed with 4 mL of brine. The ethereal layer is dried over $MgSO_4$ and evaporated to dryness. The residue is chromatographed on $SiO_2$ using 1.5% i-PrOH/$CH_2Cl_2$ as eluent on a flashchromatography column. The fractions are collected and evaporated to dryness to afford 57 mg of the title compound that is identified by mass spectrometry and nuclear magnetic resonance (NMR) spectroscopy.

EXAMPLES 2–5

Using the procedure of Example 1, the following 27-bromo compounds are prepared:

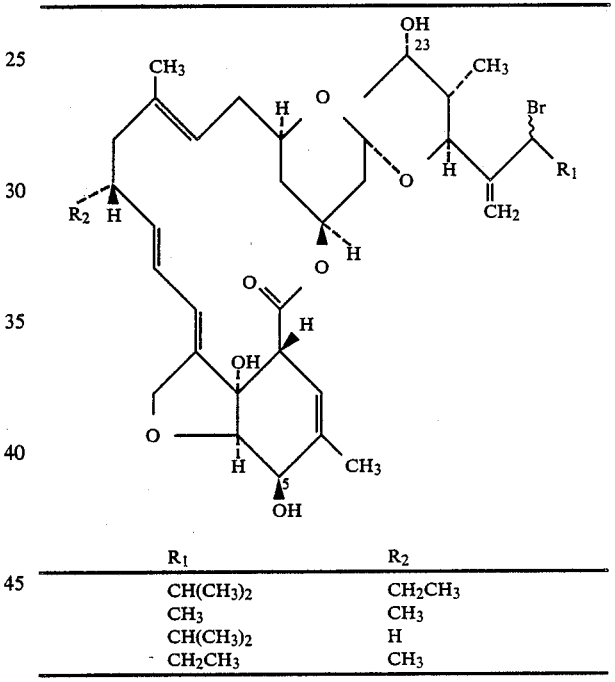

| $R_1$ | $R_2$ |
| --- | --- |
| $CH(CH_3)_2$ | $CH_2CH_3$ |
| $CH_3$ | $CH_3$ |
| $CH(CH_3)_2$ | H |
| $CH_2CH_3$ | $CH_3$ |

EXAMPLE 6

27-chloro-26-methylene-LL-F28249α

In 1 mL of methanol, N-chlorosuccinimide is stirred at 0° C. under $N_2$ atmosphere, and 130 mg of LL-F28249α in 2 mL of methanol is added dropwise. The solution is allowed to warm to room temperature and stirred for 19 hours. The reaction mixture is diluted with 30 mL of $Et_2O$ and washed successively with 5 mL of saturated $NaHCO_3$ followed by 5 mL of brine. The ethereal layer is dried ($MgSO_4$) and evaporated. The residue is purified by flash-chromatography on silica gel using 1.5%–2% i-PrOH/$CH_2Cl_2$ as eluent. The solvent is removed in vacuo from the purest fractions to afford 92.7 mg of the title compound that is identified by mass spectrometry and nuclear magnetic resonance (NMR) spectroscopy.

EXAMPLES 7-10

Using the procedure of Example 6, the following 27-chloro compounds are prepared:

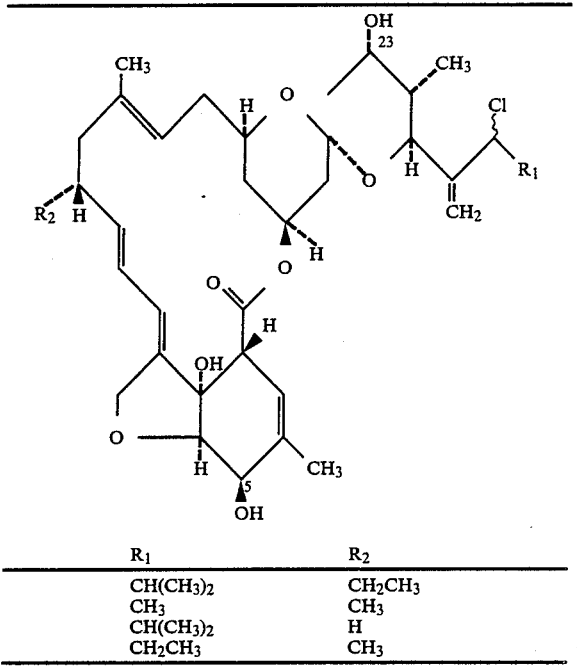

| R₁ | R₂ |
|---|---|
| CH(CH₃)₂ | CH₂CH₃ |
| CH₃ | CH₃ |
| CH(CH₃)₂ | H |
| CH₂CH₃ | CH₃ |

EXAMPLE 11

5-0-t-Butyldimethylsilyl-LL-F28249α

In 500 mL of $CH_2CL_2$, 70 g of LL-F28249α is stirred with 82.04 g of imidazole at 20° C. under $N_2$ atmosphere, and 43 g of t-butyldimethylsilyl chloride in 400 mL of $CH_2Cl_2$ is added over 5 minutes. After an hour, the reaction is assayed for completion by highperformance liquid chromatography (HPLC), using 50% $CH_3CN$/50% $H_2O$ in a curved gradient mode over 10 minutes on a Whatman Partisil CCS/C₈ rapid analysis column at 1 mL/min flowrate. Another 3 g of t-butyldimethylsilyl chloride is added, and after 3 hours the composition is 92.3% product, 0.3% LL-F28249α and 1.6% disilylated material. The mixture is diluted with $CH_2Cl_2$ and poured into 2 L of $H_2O$, and the $CH_2Cl_2$ layer is separated. The aqueous portion is extracted with 2 L of $CH_2Cl_2$, and the combined organic layers are dried ($Na_2SO_4$). The $CH_2Cl_2$ is evaporated in vacuo to afford 116 g of the title compound that is identified by mass spectrometry and nuclear magnetic resonance (NMR) spectrometry.

EXAMPLE 12

27-bromo-26-methylene-LL-F28249α

In 16 mL of acetone and 4 mL of $H_2O$, 884.5 mg of 5-0-t-butyldimethylsilyl-LL-F28249α is stirred in an ice bath, and 168.9 mg of N-bromoacetamide in 5 mL of acetone is added dropwise. The cooling bath is removed, and the reaction mixture is stirred at room temperature for 2 hours. The mixture is diluted with 100 mL of $Et_2O$, and 10 mL of brine is added. The ethereal layer is removed, dried over $MgSO_4$ and evaporated to dryness in vacuo. The residue is purified flash-chromatography on $SiO_2$ using 0.2% i-PrOH/12.5–15% EtoAc/heptane. The fractions are collected and analyzed by HPLC, and fractions 27–32 are combined and evaporated to dryness to afford the 27-bromo compound. The silyl group is then removed by stirring 101.3 mg of the above 27-bromo compound with 20.3 mg of toluenesulfonic acid in 2 mL of MeOH at 0° C. for 3 hours. The mixture is neutralized with 4 mL of saturated $NaHCO_3$ solution and extracted with 3×3 mL of $Et_2O$. The ethereal extracts are washed with brine, dried over $MgSO_4$ and evaporated to dryness. The residue is purified by flash-chromatography on $SiO_2$ using 1.5% i-PrOH in $CH_2Cl_2$ as eluent to afford 71.5 mg of the title compound, which is identical to the product of Example 1.

What is claimed is:

1. A compound represented by the formula (I):

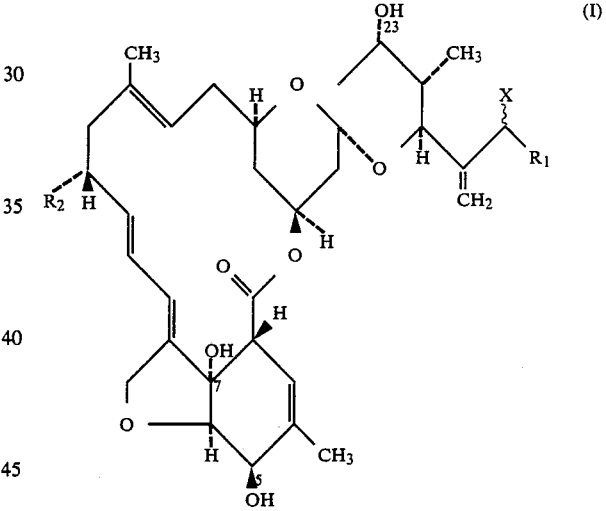

wherein, X is halogen, R₁ is methyl or isopropyl; and R₂ is hydrogen, methyl or ethyl.

2. A compound according to claim 1, wherein X is bromine or chlorine.

3. A compound according to claim 2, wherein X is bromine or chlorine; R₁ is isopropyl; and R₂ is methyl.

4. The method for the prevention, treatment or control of endoparasitic or ectoparasitic infections in warm-blooded animals, said method comprising: orally, topically or parenterally administering to an animal infected with endo- or ectoparasites, an endoor ectoparasiticidally effective amount of the compounds represented by structural formula (I),

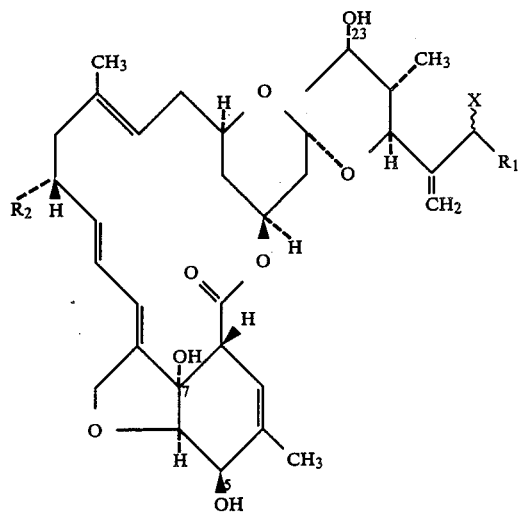

(I)

wherein, X is halogen; $R_1$ is methyl or isopropyl; and $R_2$ is hydrogen, methyl or ethyl.

5. A method according to claim 4, wherein X is halogen; $R_1$ is methyl or isopropyl; and $R_2$ is methyl or ethyl.

6. A method according to claim 5, wherein X is bromine or chlorine.

7. A method according to claim 6, wherein X is bromine, $R_1$ is isopropyl; and $R_2$ is methyl.

8. A method according to claim 6, wherein X is chlorine; $R_1$ is isopropyl; and $R_2$ is methyl.

9. A method for controlling plant insects topically or systemically, and protecting crops, trees, shrubs, stored grain and ornamentals, said method comprising: applying an insecticidally-effective amount of the compound represented by structural formula (I),

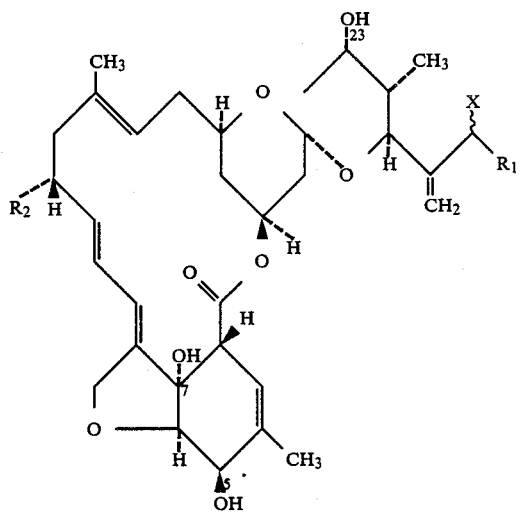

(I)

wherein X is halogen; $R_1$ is methyl or isopropyl; and $R_2$ is hydrogen, methyl or ethyl.

10. A method according to claim 9, wherein X is halogen; $R_1$ is methyl or isopropyl; and $R_2$ is methyl or ethyl.

11. A method according to claim 10, wherein X is bromine or chlorine.

12. A method according to claim 11, wherein X is bromine; $R_1$ is isopropyl; and $R_2$ is methyl.

13. A method according to claim 11, wherein X is chlorine; $R_1$ is isopropyl; and $R_2$ is methyl.

14. A method for the control of plant nematodes, said method comprising: applying to the foliage of plants, the soil in which they are grown or into the trunks thereof, a nematocidally-effective amount of the compound represented by structural formula (I),

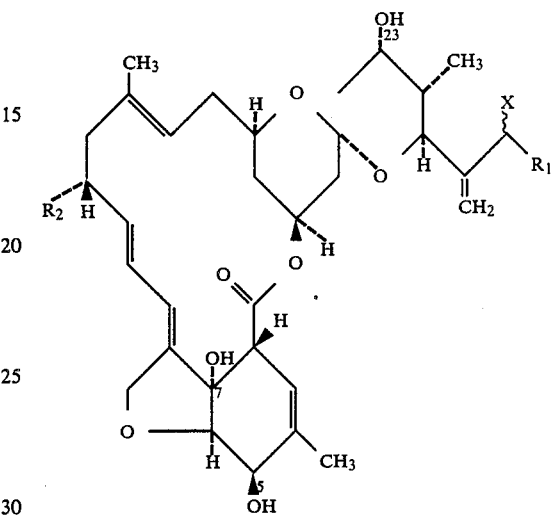

(I)

wherein, X is halogen; $R_1$ is methyl or isopropyl; and $R_2$ is hydrogen, methyl or ethyl.

15. A method according to claim 14, wherein X is halogen; $R_1$ is methyl or isopropyl; and $R_2$ is methyl or ethyl.

16. A method according to claim 15, wherein X is bromine or chlorine.

17. A method according to claim 16, wherein X is bromine; $R_1$ is isopropyl; and $R_2$ is methyl.

18. A method according to claim 16, wherein X is chlorine; $R_1$ is isopropyl; and $R_2$ is methyl.

19. A composition comprising: a prophylactically, therapeutically, pharmaceutically or insecticidally effective amount of the compound represented by structural formula (I),

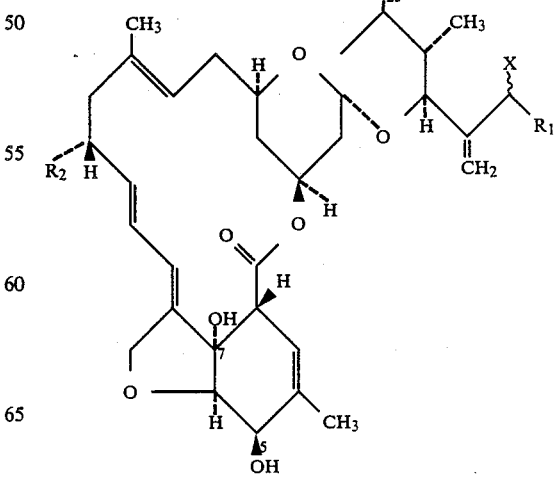

(I)

wherein, X is halogen; $R_1$ is methyl or isopropyl; and $R_2$ is hydrogen, methyl or ethyl; and an inert carrier.

20. A composition to claim 19, wherein x is halogen; $R_1$ is methyl or isopropyl; and $R_2$ is methyl or ethyl.

21. A composition according to claim 20, wherein X is bromine or chlorine.

22. A composition according to claim 21, wherein X is bromine; $R_1$ is isopropyl; and $R_2$ is methyl.

23. A composition according to claim 21, wherein X is chlorine; $R_1$ is isopropyl; and $R_2$ is methyl.

* * * * *